US006251662B1

(12) United States Patent
Day

(10) Patent No.: US 6,251,662 B1
(45) Date of Patent: Jun. 26, 2001

(54) SEALING MAT FOR MULTIWELL PLATES

(75) Inventor: Paul Francis Day, Chipstead (GB)

(73) Assignee: Advanced Biotechnologies Limited

(*) Notice: Subject to any disclaimer, the term of this patent is extended or adjusted under 35 U.S.C. 154(b) by 0 days.

(21) Appl. No.: 09/452,572

(22) Filed: Dec. 1, 1999

(30) Foreign Application Priority Data

Dec. 1, 1998 (GB) ........................................ 9826319

(51) Int. Cl.[7] ........................................ C12M 1/34

(52) U.S. Cl. ........................ 435/288.3; 435/305.3; 422/102

(58) Field of Search ........................ 422/101, 102; 435/288.3, 288.4, 305.3, 305.4

(56) References Cited

U.S. PATENT DOCUMENTS 5,342,581 8/1994 Sanadi ........................ 422/101
5,516,490 5/1996 Sanadi ........................ 422/101
5,741,463 * 4/1998 Sanadi ........................ 422/101
5,856,176 * 1/1999 Mathus et al. ............ 435/288.3

FOREIGN PATENT DOCUMENTS 0388159 3/1990 (EP) .
0747476 4/1996 (EP) .
9302290 11/1993 (WO) .
9503364 3/1995 (WO) .
9607921 5/1996 (WO) .

* cited by examiner

*Primary Examiner*—David A. Redding
(74) *Attorney, Agent, or Firm*—Galgano & Burke

(57) ABSTRACT

A plate sealing means suitable for use with multi-well plates of the type used in DNA PCR chemistry, said sealing means having a resilient mat having a flat or even surface substantially free from dimples; and an engagement structure adapted to co-operate with at least two opposing edges of the plate and adapted to retain the sealing mat in a substantially fixed position with respect to the plate.

9 Claims, 4 Drawing Sheets

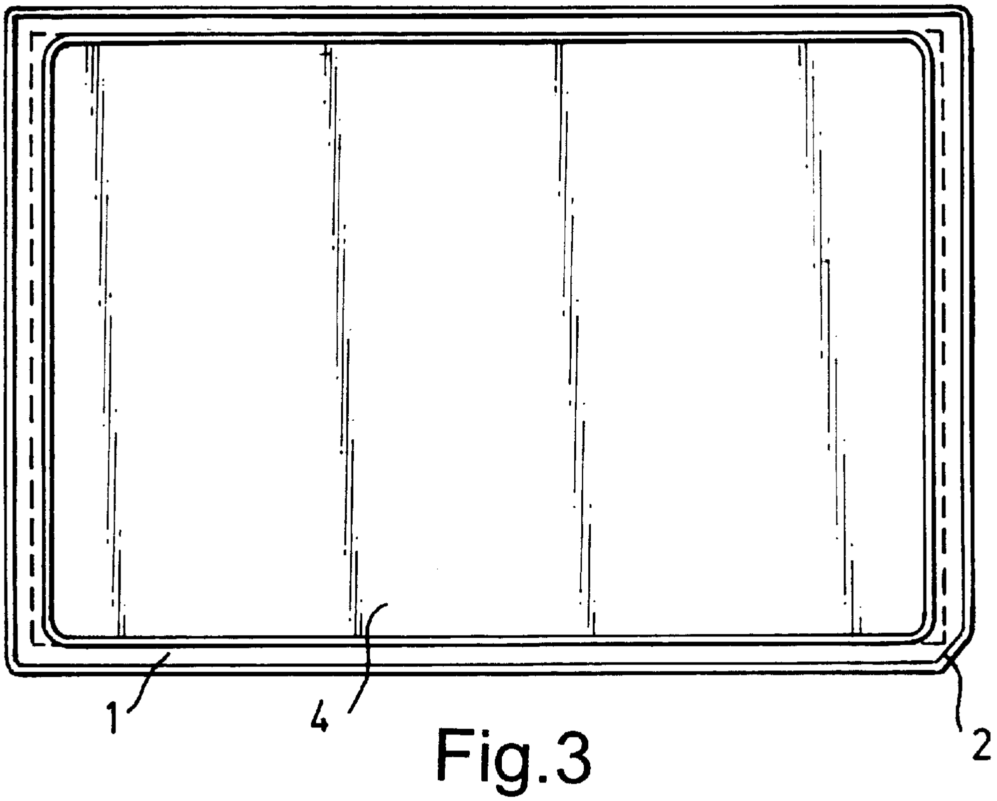
Fig.3
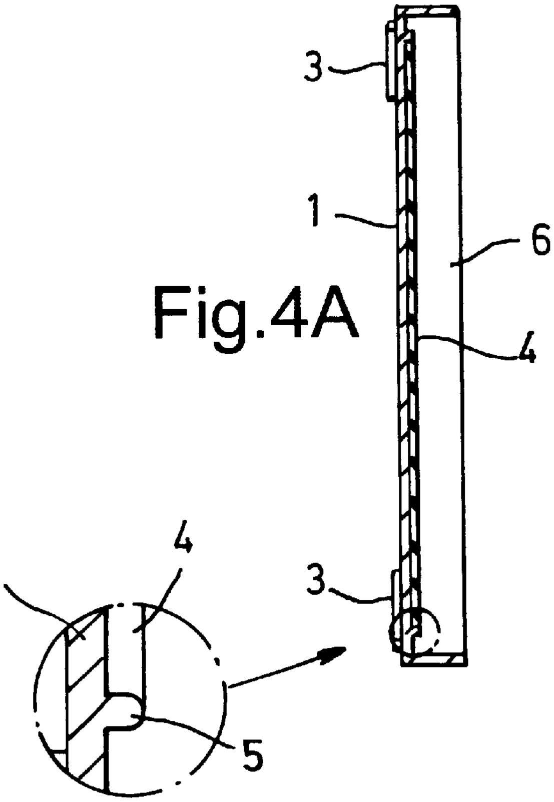
Fig.4A
Fig.4B

SEALING MAT FOR MULTIWELL PLATES

FIELD OF THE INVENTION

This invention relates to a sealing mat for multiwell laboratory plates. The invention also relates to a lid for a multiwell laboratory plate which includes a sealing mat and to a method of sealing a multiwell laboratory plate using those things.

BACKGROUND TO THE INVENTION

Multiwell plates are used extensively in molecular biology laboratories and elsewhere. One such use is in Polymerase Chain Reaction (PCR) experiments where, once filled or part filled with reagents, the plates are often sealed prior to further processing.

Multiwell plates now come in a variety of formats. 96 wells, in a 12×8 array, is one standard but now a 384 well format is becoming increasingly common. Forming a cheap, re-usable seal on these 384 plates presents a real problem.

There are a number of known ways of achieving such seals. For example, a foil or plastic film may be applied across the entire upper surface of the plate. Thus heat sealable aluminium foils or adhesive plastic films are commercially available. Once applied, these films provide an efficient, gas and liquid tight seal but are tiresome to apply and remove. Access to each well can only be obtained by piercing the film or by peeling the film off by hand or with a foil stripper. Consequently, this type of seal is not re-usable, and is not suitable for robotic application or removal.

Alternatively, a seal may be achieved by placing a relatively heavy, flexible rubber mat over the entire surface of the plate. The weight of the mat and any plates stacked on top of the mat keep the seal in place. It is important that the mat does not slide over the top of the plate in order to avoid cross-contamination. In the case of 96 well plates, this is achieved by having 96 raised pimples or "dimples" on the surface of the mat in an array which matches exactly the array of wells. Each dimple is sized and shaped to sit firmly into a well. Once in place, no lateral movement of the mat is possible because the perimeter of each dimple fits snugly within its respective well.

This arrangement is not applicable to the 384 well version because the wells are much smaller in diameter. Each dimple would need to be so small in profile that it becomes very difficult to align the mat with the wells. Even if the mat can be aligned, there is an increased tendency for the mat to slide across the top face of the wells because each dimple is correspondingly smaller than in the 96 well version.

As a further alternative, sealing caps can be applied, either in strips or as an array of 96. These sealing caps consist of individual, circular cylindrical walled caps with a pierceable lid. They fit snugly into the internal bore of each plate and each cap normally has an outer lip, which prevents it entering into the well beyond a certain point.

These caps are time-consuming to apply and require a good deal of manual dexterity on the part of the technician. Furthermore, sealing caps would be practically impossible to fit to 384 well plates, and, in any event, cannot be inserted or removed robotically.

It is therefore an objective of the present invention to overcome some or all of these disadvantages and provide an improved, re-usable sealing means applicable to all multiwell plates.

SUMMARY OF THE INVENTION

According to the present invention, there is provided a plate sealing means or cover suitable for use with multiwell plates of the type in question said sealing means comprising:

(i) a resilient sealing mat having a flat or even surface substantially free from dimples; and (ii) engagement means adapted to co-operate with at least two opposing edges of the plate and adapted to retain the sealing mat in a substantially fixed position with respect to the plate. By providing some means of engaging the mat with the side of the multiwell plate it is no longer necessary to use dimples as locators.

Preferably, the engagement means comprises a lid adapted to fit over the plate, said lid comprising a substantially flat top with depending edges, the sealing mat being located on the underside of the lid top, being the side in contact with the plate when the sealing means is in use. This provides the advantage that a multiwell laboratory plate can be quickly and effectively sealed by placing the lid onto the plate. Also, the lid can quickly and easily be removed and can be re-used. It is not necessary to accurately position any projections on the mat into wells on the multiwell plate because the mat is smooth on the surface which contacts the multiwell plate.

Preferably, the lid is substantially rigid.

In a particularly preferred embodiment, the lid further comprises locators on its uppermost-in-use surface, said locators being adapted to locate with the underside of a second plate such that the plates will stack securely one on top of each other.

Preferably, the edge of the lid incorporates apertures corresponding with holes in the plate, said holes being provided to facilitate robotic plate positioning and removal from a thermal cycle block. Robotic operation is particularly important when large numbers of plates have to be handled. The plates must still be capable of robotic manipulation even when the lids are in place.

In an alternative embodiment, the engagement means comprises a series of lugs projecting from the sealing mat and adapted to engage with holes in the plate, said holes being provided to facilitate robotic plate positioning and removal from a thermal cycler block.

Preferably the lugs are resiliently flexible.

Preferably the lugs project outwardly from the edges of the mat in the plane of the mat.

In a particularly preferred embodiment the sealing mat and the lugs are of unitary construction.

Preferably the sealing mat is made from neoprene or silicone rubber.

In order that the invention may be better understood, preferred embodiments will now be described, by way of example only, with reference to the accompanying schematic drawings, in which:

FIG. 3 shows a plan view from below of the lid of FIG. 1;

FIG. 4A shows a cross-sectional view along line B—B of FIG. 1;

FIG. 4B is an enlargement of a detail in FIG. 4A;

DESCRIPTION OF THE PREFERRED EMBODIMENTS

Preferred embodiments of the present invention will now be more particularly described by way of example only. These are currently the best ways known to the Applicant of putting the invention into practice, but they are not the only ways in which this can be achieved.

Figure 1:
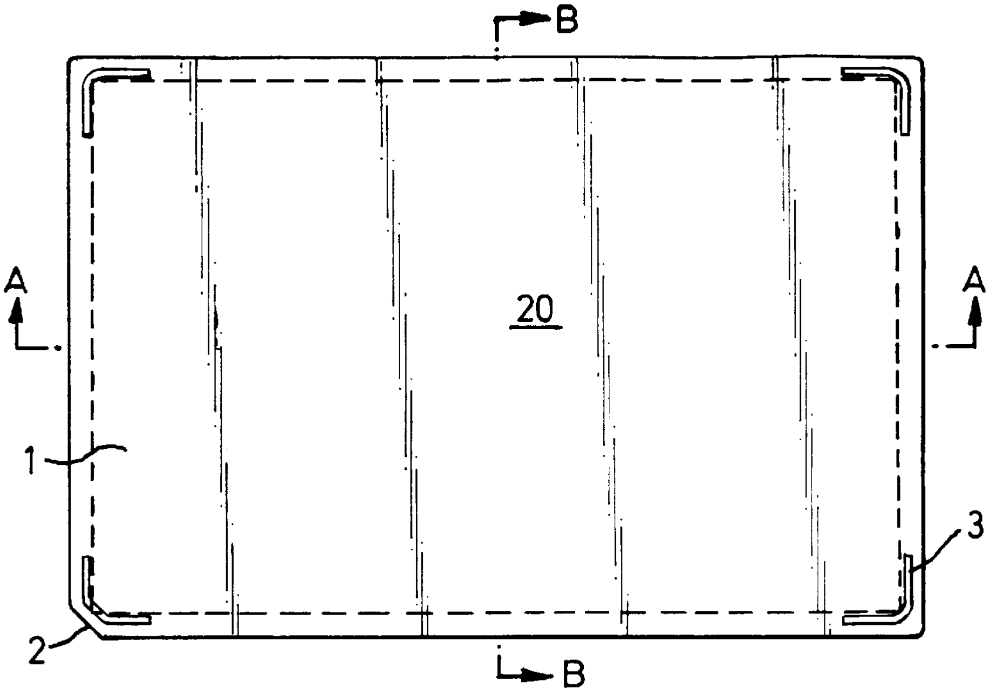
FIG. 1 illustrates a plan view from above of a lid for a multiwell plate according to a first embodiment of the invention.

FIG. 1 illustrates a plan view from above of a sealing means 20 for a multiwell plate. The sealing means or cover consists of a substantially rectangular lid 1 with dependent edges 7 into which is fitted a sealing mat 4. The dependent edges retain the sealing mat in place over a plate. One corner of the lid has a chamfered corner 2 which acts as an orientation marker and is adapted to fit a correspondingly shaped cut-away on the corner of a PCR plate. The dimensions of the chamfered corner 2 are dictated in part by the dimensions of the plate.

The lower or inner surface of the lid 1 is substantially flat or planar and the lower surface of the sealing mat 4 is also correspondingly flat and smooth. This is an important feature of the present invention because it avoids the need for any dimples to locate in the wells.

The top of lid 1 may incorporate projections or recesses 3 which act as locators for the bottom of another plate. Thus, in the case of a skirted plate, the projections take the form of rims 3 at each corner of the lid into which the skirt of another plate will fit. This is illustrated more clearly in FIGS. 2A and 2B. Once again, the rim at one corner is angled to correspond with a cut-away on the plate.

Once a multiwell plate is sealed with a lid 20 then several other lidded plates can be stacked one or top of each other using the locators to hold the stack in place.

It is not necessary for the rim to be continuous around the perimeter of the lid although this is possible.

If the plates are not skirted then some other form of projection or indentation can be provided to retain the bottom of the outer walls of the plate above. This disclosure is intended to encompass any suitable locator adapted for this purpose.

The edges of the lid are an important feature of this invention. Not only do they retain the cover in a snug positional fit with the plate beneath, but they also provide access for robotic arms, which typically manipulate these plates. Thus, in at least two of the sides 6 of the lid, gaps or apertures 9 are provided to enable the covered plate to be picked up by a robotically controlled lifting apparatus as is known in the art. These gaps 9 in the sides 6 of the lid correspond with holes in the side of a multiwell laboratory plate so that in use, when the lid is in place, it is still possible to insert the fingers of a robotically controlled arm into these holes. The apertures 9 are large enough to enable the lid to be used with a variety of different multiwell laboratory plates from different manufacturers, which inevitably have holes in a slightly different location.

Figure 2A:
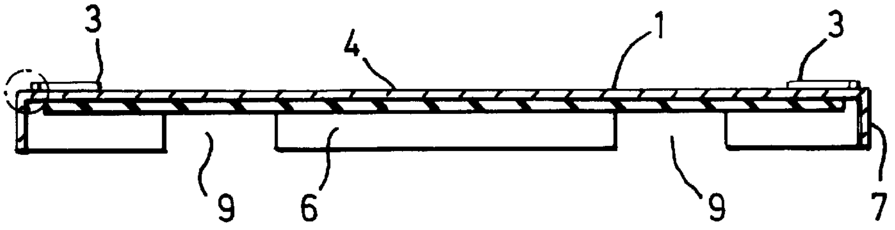
FIG. 2A shows a cross-section along line A—A of FIG. 1.
Figure 2B:
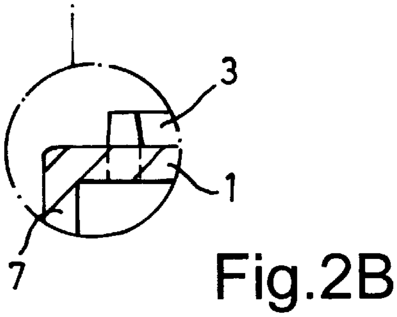
FIG. 2B is an enlargement of a detail in FIG. 2A.
Figure 5A:
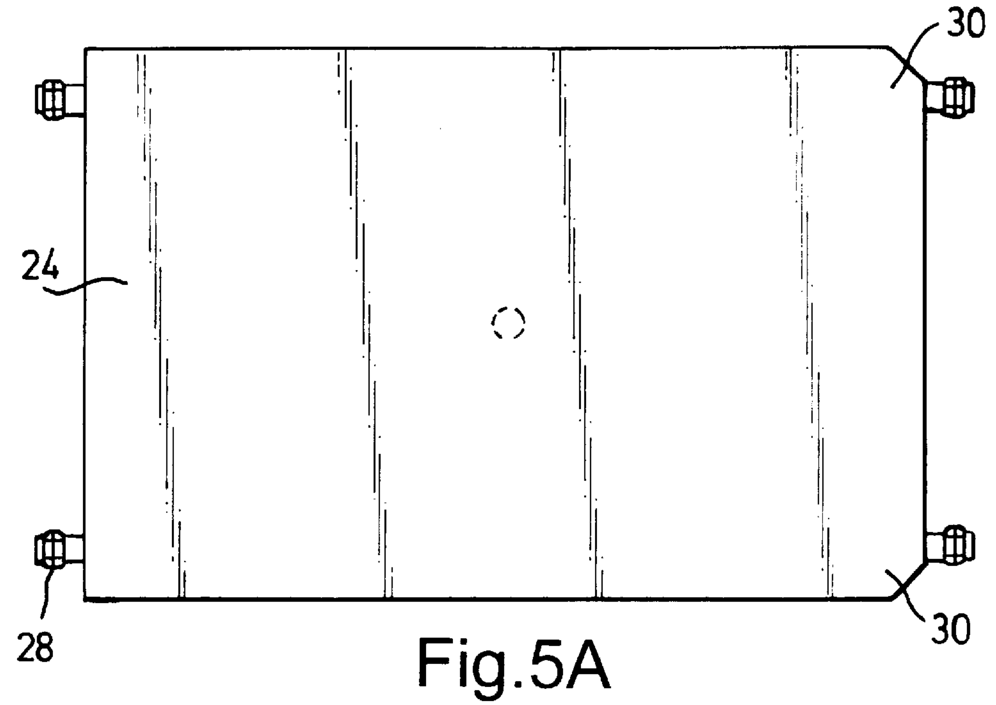
FIGS. 5A, 5B and 5C illustrate plan, side and end elevations of a sealing mat according to a second aspect of the invention.
Figure 5B:
Figure 5C:
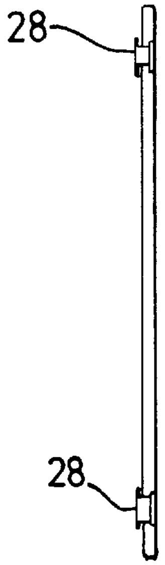

FIG. 2A is a cross-section along line A—A of FIG. 1 and shows how a sealing mat 4 is fixed to the underside of the lid. In this example, the sealing mat is made from neoprene rubber although any other suitable material as selected by the materials specialist, such as silicone rubber, can be used. The lid 1 has sides 6, 7 which extend in use over the rim of the multiwell plate (not shown). The sealing mat 4 can be fixed to the underside of the lid in any suitable manner, for example, using glue or other adhesive.

FIG. 3 is a plan view from below of the lid of FIG. 1. This shows the sealing mat 4 on the underside of the lid.

FIG. 4A is a cross-section along the line B—B of FIG. 1, and also shows the locator projections 3. In this example the sealing mat is located by lugs 5 on the underside of the lid. These lugs make it easier to locate the mat in the correct position during assembly. They also ensure that the mat is fixed centrally over the plate.

FIG. 4B shows one of the lugs 5 in more detail on the underside of the lid which retain the mat 4 in place and ensure that it is fixed into the correct position inside the lid. Once the sealing mat 4 is fixed to the underside of the lid, then the cover 20 can simply be placed onto a multiwell plate in order to seal the plate. It is not necessary for the mat 4 to incorporate any dimples for locating into the tops of the wells in the plate and this makes it easier to position the lid and mat in place. Also, the mat 4 cannot slip or move about on the plate because it is held in place by the lid, which has sides 6, 7 that locate around the rim of the multiwell plate. This avoids any possible cross-contamination of the contents of adjacent wells.

The terms sides or edges in this context have a very broad meaning. The terms are intended to encompass any form of restraint which keeps the cover in place when it is over a multiwell plate. It is certainly not necessary that the sides or edges should extend around substantially the whole of the lid although this may be desirable.

It will be appreciated that the combination of the lid 1 and the sealing mat 4 comprises a sealing means for sealing such plates. The edges of the lid act as an engagement means, which co-operates with at least two opposing edges of a multiwell plate to retain the sealing mat in a substantially fixed position with respect to the plate itself. The sealing mat is made of any suitable resilient material, which enables it to deform around the mouth of each well and thus form an effective seal.

Figure 6A:
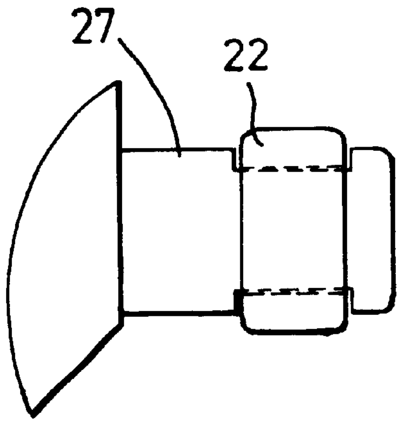
FIGS. 6A, 6B and 6C illustrate plan, side and end elevations of a lug from FIG. 5.
Figure 6C:
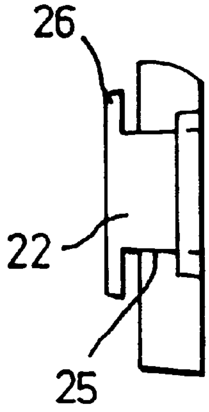
Figure 6B:
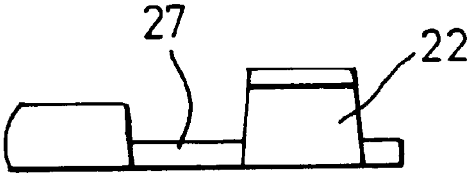
Figure 7A:
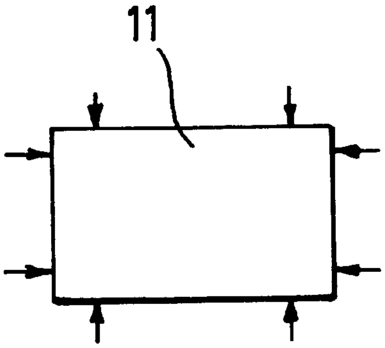
FIG. 7A shows diagrammatically the location of robotic arm locator holes.
Figure 7B:
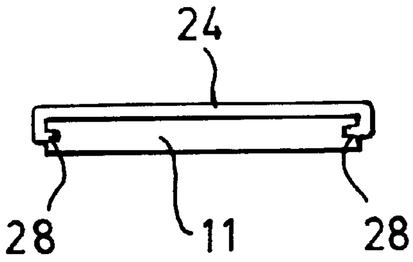
FIG. 7B shows how the lugs of this embodiment flex over to locate in the robotic arm locator holes.

A further embodiment 30 of the present invention is illustrated in FIGS. 5A–5C and 6A–6C. A resiliently flexible sealing mat 24 is provided with projections or lugs 28 which are so sized and shaped as to fit into some of the robotic location holes in a skirted multiwell plate. At least one corner 30 of the sealing mat 24 is chamfered in order to assist in the orientation of the mat 24. This type of sealing mat 24 is used together with a multiwell laboratory plate of the type with robotic handling holes as illustrated in FIG. 7A. FIG. 7A is a schematic plan view of a multiwell laboratory plate 11, which has at least eight robotic locator holes in its sides. The position of these robotic locator holes is indicated by the arrows.

The sealing mat 24 and lugs 28 are preferablyy of unitary construction being formed from a single piece of resiliently flexible material such as neoprene or silicone rubber. In use, the projections 28 are bent over the rim of the multiwell plate 11 and inserted into four of the robotic locator holes in the sides of the skirt of the plate. The projections each have a head 22 as shown in FIGS. 6A–6C. These heads are slightly larger than the robotic locator holes. However, because the projections 28 are made of flexible, resiliently deformable material, the heads can be squeezed through the robotic locator holes. This secures the mat 24 to the multiwell laboratory plate 11 and creates an effective seal. Other multiwell laboratory plates that have been sealed in this way can be stacked one on top of each other. The sealing mats 24 are preferably made from rubber or other suitable material which has a non-slip surface which helps to prevent the plates in a stack moving in respect to one another.

The shape and configuration of the lugs are an important feature of this invention. The head of each lug is spaced from the body of the mat by a neck 27. The lug has a head region 22, which is generally thicker than the body of the mat to which it is attached. A retaining section 26 creates what is, in effect, a resiliently flexible headed stud with an undercut waist region 25. This arrangement is so sized and shaped that the retaining section 26 will just pass through the robotic locator holes in the skirt of the plate but will not immediately slip back. The sealing mat is therefore retaining in sealing contact with the plates until the retaining section 26 is resiliently deformed to withdraw it from the hole.

It will thus be appreciated that the lugs from an engagement means adapted to co-operate with at least two opposing edges of the plate to which the sealing cover is to be attached and which are adapted to retain the sealing mat in a substantially fixed position with respect to the plate.

The covers of the present invention can be formed from a wide variety of materials as selected by the material specialist. For example, the lids can be formed from any suitable substantially rigid plastics material such as polyethylene, polypropylene, polyvinylchloride, polystyrene or polycarbonate. Neoprene or silicone rubbers are suitable materials for use in the sealing mat.

What is claimed is:

1. A plate sealing means suitable for use with multiwell plates of the type used in DNA PCR chemistry, said sealing means comprising:

(i) a resilient sealing mat having a flat surface substantially free from dimples; and (ii) engagement means adapted to cooperate with at least two opposing edges of the plate and adapted to retain said sealing mat in substantially fixed position with respect to said plate, wherein said engagement means comprises a lid adapted to fit over said plate, said lid comprising a substantially flat top with depending edges, said sealing mat being located on the underside of said lid top, being the side in contact with said plate when the sealing means is in use and wherein the edge of the lid incorporates apertures corresponding with holes in said plate, said holes being provided to facilitate robotic plate positioning and removal from a thermal cycler block.

2. A plate sealing means as claimed in claim 1 wherein the lid is substantially rigid.

3. A plate sealing means as claimed in claim 1 wherein the lid further comprises locators on its uppermost-in-use surface, said locators being adapted to locate with the underside of a second plate such that the plates will stack securely one on top of each other.

4. A plate sealing means suitable for use with multiwell plates of the type used in DNA PCR chemistry, said sealing means comprising:

(i) a resilient sealing mat having a flat surface substantially free from dimples; and (ii) engagement means adapted to cooperate with at least two opposing edges of the plate and adapted to retain said sealing mat in a substantially fixed position with respect to the plate;

wherein the engagement means comprises a series of lugs projecting from said sealing mat and adapted to engage with holes in the plate, said holes being provided to facilitate robotic plate positioning and removal from a thermal cycler block.

5. A plate sealing means according to claim 4 wherein the lugs comprise a head region spaced from the body of the sealing mat by a neck, the head region being thicker than the body of the mat to which it is attached.

6. A plate sealing means as claimed in claim 4 wherein the lugs are resiliently flexible.

7. A plate sealing means as claimed in claim 4 wherein the lugs project outwardly from the edges of the mat in the plane of the mat.

8. A plate sealing means as claimed in claim 4 wherein the sealing mat and the lugs are of unitary construction.

9. A plate sealing means as claimed in claim 4 wherein the sealing mat is made from neoprene rubber.

* * * * *